US012632956B2

(12) United States Patent
Saito et al.

(10) Patent No.: US 12,632,956 B2
(45) Date of Patent: May 19, 2026

(54) FUNDUS IMAGE PROCESSING DEVICE AND NON-TRANSITORY COMPUTER-READABLE STORAGE MEDIUM STORING COMPUTER-READABLE INSTRUCTIONS

(71) Applicants: NATIONAL UNIVERSITY CORPORATION HOKKAIDO UNIVERSITY, Sapporo (JP); NIDEK CO., LTD., Gamagori (JP)

(72) Inventors: Michiyuki Saito, Sapporo (JP); Kousuke Noda, Sapporo (JP); Kanae Fukutsu, Sapporo (JP); Susumu Ishida, Sapporo (JP); Ryosuke Shiba, Gamagori (JP); Yoshiki Kumagai, Gamagori (JP)

(73) Assignees: NATIONAL UNIVERSITY CORPORATION HOKKAIDO UNIVERSITY, Sapporo (JP); NIDEK CO., LTD., Gamagori (JP)

( * ) Notice: Subject to any disclaimer, the term of this patent is extended or adjusted under 35 U.S.C. 154(b) by 551 days.

(21) Appl. No.: 17/826,884

(22) Filed: May 27, 2022

(65) Prior Publication Data

US 2022/0284577 A1    Sep. 8, 2022

Related U.S. Application Data

(63) Continuation of application No. PCT/JP2020/043913, filed on Nov. 25, 2020.

(30) Foreign Application Priority Data

Nov. 29, 2019    (JP) ................................. 2019-216265

(51) Int. Cl.
G16H 30/40    (2018.01)
A61B 3/14    (2006.01)
G06T 7/00    (2017.01)

(52) U.S. Cl.
CPC .............. G06T 7/0012 (2013.01); A61B 3/14 (2013.01); G16H 30/40 (2018.01);
(Continued)

(58) Field of Classification Search
CPC ......... G06T 7/0012; G06T 2207/20081; G06T 2207/20084; G06T 2207/30041;
(Continued)

(56) References Cited

U.S. PATENT DOCUMENTS 6,996,260 B1    2/2006 Skands et al.
2011/0007271 A1*    1/2011 Ono .......................... G06T 5/50
351/206
(Continued)

FOREIGN PATENT DOCUMENTS

CN    102982314 A    *    3/2013    ........... G06K 9/4604
CN    107657612 A    *    2/2018    ........... G06T 7/0012
(Continued)

OTHER PUBLICATIONS

He et al.; "Association between blood pressure and retinal arteriolar and venular diameters in Chinese early adolescent children, and whether the association has gender difference: a cross sectional study;" BMC Ophthamology; 2018; pp. 1-12; vol. 18, No. 133.
(Continued)

*Primary Examiner* — Huo Long Chen
(74) *Attorney, Agent, or Firm* — Oliff PLC

(57)    ABSTRACT

A processor of a fundus image processing device acquires a fundus image 50 photographed by a fundus image photographing device. The processor acquires blood vessel images 60A and 60B that indicate at least one of an arteriole
(Continued)

and a venule in the fundus image 50 by inputting the fundus image 50 into a mathematical model trained by a machine learning algorithm. The processor acquires a blood vessel area that is an area of at least one of the arteriole and the venule in the whole of the blood vessel images 60A and 60B.

4 Claims, 13 Drawing Sheets

(52) U.S. Cl.
   CPC .............. *G06T 2207/20081* (2013.01); *G06T 2207/20084* (2013.01); *G06T 2207/30041* (2013.01); *G06T 2207/30101* (2013.01)

(58) Field of Classification Search
   CPC . G06T 2207/30101; G06T 2207/10101; G06T 2207/20076; G06T 2207/30168; A61B 3/14; A61B 3/102; A61B 3/0025; A61B 3/1241; G16H 30/40
   See application file for complete search history.

(56)                References Cited

U.S. PATENT DOCUMENTS

| | | |
|---|---|---|
| 2012/0236259 A1 | 9/2012 | Abramoff et al. |
| 2014/0294235 A1 | 10/2014 | Ishida et al. |
| 2015/0374228 A1 | 12/2015 | Satake et al. |
| 2017/0258296 A1* | 9/2017 | Kaku .................... A61B 1/044 |

| | | |
|---|---|---|
| 2017/0316165 A1 | 11/2017 | Brauner et al. |
| 2018/0235527 A1* | 8/2018 | Yamamoto ......... A61B 1/00188 |
| 2019/0059718 A1 | 2/2019 | Abramoff et al. |
| 2020/0118681 A1 | 4/2020 | Brauner et al. |

FOREIGN PATENT DOCUMENTS

| | | | | |
|---|---|---|---|---|
| CN | 110135528 A | * | 8/2019 | ............... A61B 3/14 |
| CN | 110335254 A | * | 10/2019 | ........... G06K 9/6268 |
| CN | 110443813 A | * | 11/2019 | ........... G06F 18/253 |
| JP | H07-210655 A | | 8/1995 | |
| JP | 2002-542863 A | | 12/2002 | |
| JP | 2014-504523 A | | 2/2014 | |
| JP | 2014-193225 A | | 10/2014 | |
| JP | 2017-077414 A | | 4/2017 | |
| JP | 2018-171177 A | | 11/2018 | |
| JP | 2019-514575 A | | 6/2019 | |

OTHER PUBLICATIONS

Jan. 19, 2021 Search Report issued in International Patent Application No. PCT/JP2020/043913.
May 17, 2022 International Preliminary Report on Patentability issued in International Patent Application No. PCT/JP2020/043913.
Apr. 30, 2025 Office Action issued in Japanese Patent Application No. 2021-561470.
Yamamoto, Yuuka, et al., Age-Related Decrease of Retinal Vasculature Area Identified with a Novel Computer-Aided Analysis System, Tohoku J. Exp. Med., 2012, pp. 228,229-237.

* cited by examiner

| | R | 95% CONFIDENTIAL INTERVAL | | p | |
|---|---|---|---|---|---|
| Arteriolar area (AA) | −0.40 | −0.46 | −0.33 | 2.20E−16 | |
| SEX | 0.20 | 0.13 | 0.27 | 1.43E−07 | |
| SYSTOLIC BLOOD PRESSURE | 0.48 | 0.42 | 0.53 | 2.20E−16 | |
| AGE | 0.57 | 0.52 | 0.62 | 2.20E−16 | |
| SEX + SYSTOLIC BLOOD PRESSURE + AGE | 0.68 | 0.64 | 0.72 | 2.20E−16 | * |
| AA + SEX + SYSTOLIC BLOOD PRESSURE + AGE | 0.70 | 0.66 | 0.73 | 2.20E−16 | * |

$P$ = 2.2e-16
R = 0.70

MEASURED VALUE OF baPWV

FUNDUS IMAGE PROCESSING DEVICE AND NON-TRANSITORY COMPUTER-READABLE STORAGE MEDIUM STORING COMPUTER-READABLE INSTRUCTIONS

CROSS REFERENCE TO RELATED APPLICATION

This application is a continuation application of International Application No. PCT/JP2020/043913, filed Nov. 25, 2020, which claims priority from Japanese Patent Application No. 2019-216265, filed Nov. 29, 2019. The disclosure of the foregoing applications is hereby incorporated by reference in their entirety.

BACKGROUND

The present disclosure relates to a fundus image processing device and a non-transitory computer-readable storage medium storing computer-readable instructions that process a fundus image of a subject eye.

A state of a blood vessel of a living body can be recognized by observing a fundus without invading a subject eye. Conventionally, information relating to a blood vessel (an arteriole and/or a venule) acquired from a fundus image has been utilized for various diagnoses. For example, in a method for measuring the arteriole-venule diameter ratio disclosed in Japanese Unexamined Patent Application Publication No. 2014-193225, a plurality of regions $R_n$ surrounded by two concentric circles having different radiuses are defined around an optic papilla (hereinafter, simply referred to as a papilla) as a center point. A plurality of blood vessels is extracted from the defined region $R_n$. Two blood vessels having the smallest distance therebetween are selected from the extracted blood vessels, as a blood vessel pair. The arteriole-venule diameter ratio is calculated based on the selected blood vessel pair.

SUMMARY

The method disclosed in Japanese Unexamined Patent Application Publication No. 2014-193225 refers to only the blood vessel within some regions around the papilla, and thus reliability and accuracy of the information to be acquired might be inferior. It may be considered to acquire the information from an image of the fundus including tissues other than the blood vessel. However, in such a case, a disease of the fundus, opacity of the subject eye, and an artifact in the image are liable to affect the information to be acquired. Thus, the conventional technique is difficult to appropriately acquire the information based on the blood vessel of a living body, from the fundus image.

Embodiments of the broad principles derived herein provide a fundus image processing device and a non-transitory computer-readable storage medium storing computer-readable instructions that are capable of appropriately acquiring information based on blood vessel of a living body, from a fundus image.

Embodiments of a first aspect provide a fundus image processing device that processes a fundus image of a subject eye. A processor of the fundus image processing device performs the steps of: (a) acquiring the fundus image photographed by a fundus image photographing device (also referred to as "a fundus image acquiring step"); (b) acquiring a blood vessel image that indicates at least one of an arteriole and a venule in the fundus image by inputting the fundus image into a mathematical model trained by a machine learning algorithm (also referred to as "a blood vessel image acquiring step"); and (c) acquiring a blood vessel area that is an area of at least one of the arteriole and the venule in the whole of the blood vessel image acquired in the blood vessel image acquiring step (also referred to as "a blood vessel area acquiring step").

Embodiments of a second aspect provide a non-transitory computer-readable storage medium storing computer-readable instructions executed by a processor of a fundus image processing device that processes a fundus image of a subject eye. When executed by the processor of the fundus image processing device, the instructions causes the fundus image processing device to perform the steps of: (a) acquiring the fundus image photographed by a fundus image photographing device (the fundus image acquiring step); (b) acquiring a blood vessel image that indicates at least one of an arteriole and a venule in the fundus image by inputting the fundus image into a mathematical model trained by a machine learning algorithm (the blood vessel image acquiring step); and (c) acquiring a blood vessel area that is an area of at least one of the arteriole and the venule in the whole of the blood vessel image acquired in the blood vessel image acquiring step (the blood vessel area acquiring step).

According to the fundus image processing device and the non-transitory computer-readable storage medium storing the computer-readable instructions, the information based on blood vessel of a living body can be appropriately acquired from a fundus image.

BRIEF DESCRIPTION OF THE DRAWINGS

FIG. 9 shows graphs relating to the arteriolar area and the venular area as the systolic blood pressure is set in the horizontal axis and the blood vessel area is set in the vertical axis.

FIG. 12 is a table showing a correlation between the PWV and either of the arteriolar area (AA), sex, systolic blood pressure and age of a subject.

DETAILED DESCRIPTION

Figure 1:
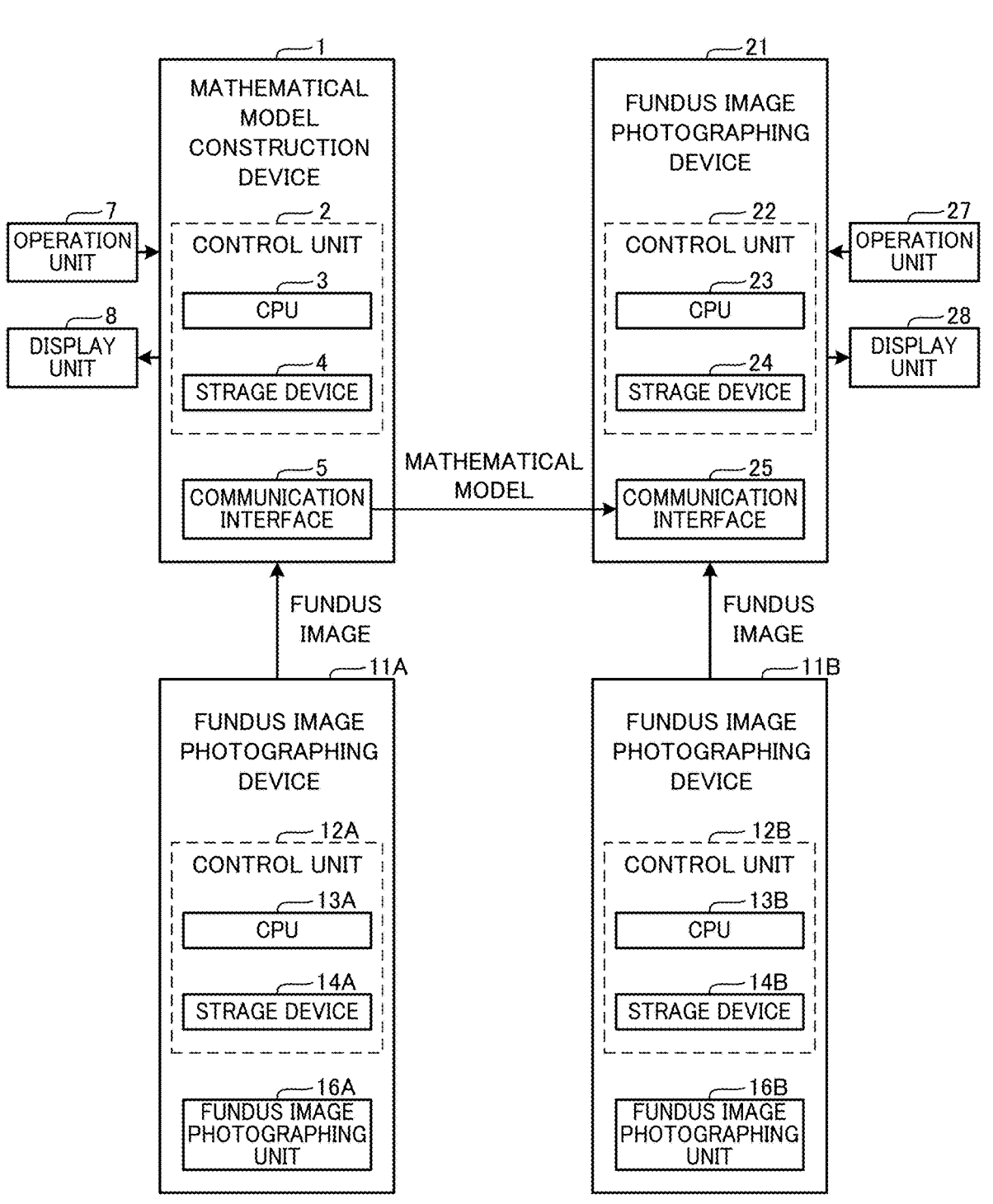
FIG. 1 is a block diagram illustrating a schematic configuration of a mathematical model construction device 1, a fundus image processing device 21, and fundus image photographing devices 11A and 11B.

A processor of a fundus image processing device exemplarily described in the present disclosure executes the steps of: (a) the fundus image acquiring step; (b) the blood vessel image acquiring step; and (c) the blood vessel area acquiring step. In the blood vessel image acquiring step, the processor acquires the blood vessel image that indicates at least one of an arteriole and a venule in the fundus image by inputting the fundus image into a mathematical model trained by a machine learning algorithm. In the blood vessel area acquiring step, the processor acquires the blood vessel area that is an area of at least one of the arteriole and the venule in the whole of the blood vessel image acquired in the blood vessel image acquiring step.

According to the fundus image processing device exemplarily described in the present disclosure, an area of a blood vessel within a wide region on a fundus can be acquired, compared to a configuration that refers to only the blood vessel within a part of the region on the fundus (for example, a region around an optic papilla). Thus, highly reliable and accurate information can be acquired from the fundus blood vessel. Further, the blood vessel area can be acquired from the blood vessel image acquired based on the fundus image, which is different from a configuration that acquires information from the whole image of the fundus including a tissue in addition to the blood vessel. Accordingly, a disease of the fundus within the fundus image, opacity of the subject eye, and an artifact in the image hardly affect the information to be acquired. Consequently, the information based on the blood vessel of a living body can be appropriately acquired from the fundus image.

Various types of fundus image having the fundus blood vessel therein may be used as the fundus image to be input into the mathematical model. For example, a two-dimensional fundus image generated by photographing a fundus from a front side thereof, using a fundus camera may be input into the mathematical model. In this case, the blood vessel image may be acquired from a color fundus image. Further, a two-dimensional optical coherence tomography (OCT) angiographic image of the fundus photographed by an OCT device may be input into the mathematical model. The OCT angiographic image may be a motion-contrast image generated by processing at least two OCT signals relating to the same portion acquired at different times. The OCT device can photograph the OCT angiographic image of which the resolution is higher than that of the other types of fundus image. Thus, by acquiring the blood vessel image from the OCT angiographic image, the accuracy and reliability of the information based on the blood vessel of a living body can be further improved. A two-dimensional fundus image photographed by a scanning laser ophthalmoscope (SLO) from the front side of the fundus may be input into the mathematical model. A two-dimensional front image, or a three-dimensional tomographic image of the fundus photographed by the OCT device may be input into the mathematical model.

The processor may further execute the step of (d) outputting an index (also referred to as "a subject index") that indicates at least one of an estimated age of the subject for which the fundus image is photographed, a degree of hypertension, and a degree of arteriosclerosis, based on the blood vessel area acquired in the blood vessel area acquiring step (also referred to as "an index outputting step"). The present inventors found that there is a correlation between the blood vessel area in the fundus of the subject and the age and the blood pressure of the subject. A state of the arteriosclerosis due to the hypertension, hyperlipidemia or the like of the subject is shown in the fundus blood vessel. Thus, by using the blood vessel area acquired in the blood vessel area acquiring step, the index that indicates at least one of the estimated age of the subject, a degree of hypertension, and a degree of arteriosclerosis can be appropriately output without diagnosis of a skillful doctor.

However, the fundus image processing device may output only the acquired blood vessel area without outputting the subject index. Also in this case, an operator can easily and appropriately perform the diagnosis of the subject based on the information of the blood vessel area to be output.

An image region of the fundus image to be input into the mathematical mode may be set to include an optic papilla and a macula of a subject eye. This case refers to information of the blood vessel in a region larger than the fundus, so that the reliability and the accuracy of the information to be acquired (for example, at least one of the blood vessel area and the subject index) can be further improved, compared to a case that refers to the information of the blood vessel in a narrow region (for example, a region only around an optic papilla).

The processor may further execute the step of adjusting an area (also referred to as "an area adjusting step") to be close to a target value by adjusting the area of the image region from which the blood vessel area is acquired in the blood vessel area acquiring step. In this case, the area of the image region from which the blood vessel area is acquired can be uniformized, so that an influence of the individual difference of the subject eyes and the difference of the photographing ways can be suppressed. Consequently, the reliability and the accuracy of the information to be acquired can be further improved.

A specific method for executing the area adjusting step may be appropriately selected. For example, an area of a region on a fundus to be photographed is changed based on an eye axial length of a subject eye to be photographed even in a case in which a photographing field angle is identical. Thus, the processor may adjust the area of the region of the fundus image or the blood vessel image from which the blood vessel area is acquired based on the eye axial length of the subject eye to be photographed. Further, the fundus blood vessel branches off several times in the way going away from the optic papilla. The processor may set a region including the fundus blood vessel from the optic papilla to the N-th (N is a natural number set in advance) branch point within the fundus blood vessel, as the region of the fundus image or the blood vessel image from which the blood vessel area is acquired. Further, the processor may adjust the area of the region on the fundus from which the blood vessel area is acquired by inputting the fundus image photographed at the identical photographing field angle, into the mathematical model. Also in this case, the reliability and the accuracy of the information to be acquired can be improved, compared to a case using the fundus images photographed at different photographing field angles. In the area adjusting step, the area of the region of the fundus image to be input into the mathematical model may be adjusted, or alternatively the area of the region of the blood vessel image from which the blood vessel area is acquired may be adjusted.

The processor may further execute the step of eliminating (also referred to as "an eliminating step") the fundus image of which a focusing score in photographing is less than a criterion, from the fundus image to be input into the mathematical model in the blood vessel image acquiring step. In the fundus image of which the focusing score is less than a criterion, an area of the blood vessel in the fundus image is larger than the actual blood vessel area. Thus, the reliability and the accuracy of the information to be acquired can be further improved by executing the eliminating step.

A specific method for executing the eliminating step may be appropriately selected. For example, in the fundus image of which the focusing score is low, the edge of the image is unsharp. Thus, the processor may execute an edge detection processing to the fundus image through an image processing and then eliminate the fundus image of which the edge sharpness is less than a threshold.

The processor may input the fundus image of which the focusing score is the highest, into the mathematical model in the blood vessel image acquiring step, among a plurality of the fundus images generated by photographing the fundus of the single subject eye while changing the focus. Also in this case, the reliability and the accuracy of the information to be acquired can be appropriately improved.

The mathematical model may be trained by the fundus image of the subject eye photographed in advance, the fundus image serving as an input training data, and the blood vessel image indicating at least one of the arteriole and the venule in the fundus image in the input training data, the blood vessel image serving as an output training data. In this case, the blood vessel image can be appropriately acquired through a simple processing, compared to, for example, a method for detecting the blood vessel and then classifying the blood vessel into the arteriole or the venule.

The input training data and the output training data used for training the mathematical model may be appropriately selected. For example, as described above, the two-dimensional color front image of the fundus photographed by the fundus camera may be used as the input training data. Or alternatively, the two-dimensional front image of the fundus photographed by the SLO may be used as the input training data. Further, a blood vessel image manually generated by an operator by referring to the fundus image photographed by the fundus image photographing device may be used as the output training data. Further, a provisional blood vessel image may be acquired by inputting the fundus image into a provisional mathematical model that outputs the blood vessel image when the fundus image is input thereto, and then the acquired provisional blood vessel image may be modified by the operator to generate the input training data. In this case, the mathematical model is further appropriately trained, so that the accuracy of the blood vessel image to be acquired can be improved.

Device configuration One typical embodiment of the present disclosure is now described with reference to the drawings. As shown in FIG. 1, this embodiment employs a mathematical model construction device 1, a fundus image processing device 21, and fundus image photographing devices 11A and 11B. The mathematical model construction device 1 constructs a mathematical model by training a mathematical model using a machine learning algorism. A program that executes the constructed mathematical model is stored in a storage device 24 of the fundus image processing device 21. The fundus image processing device

21 inputs a fundus image into the mathematical model so as to acquire an image (blood vessel image) that indicates at least one of an arteriole and a venule within the fundus image. Further, the fundus image processing device 21 acquires an area (blood vessel area) of at least one of the arteriole and the venule within the whole of the blood vessel image. Further, the fundus image processing device 21 outputs a subject index that indicates at least one of an estimated age of the subject for which the fundus image has been photographed, a degree of hypertension, and a degree of arteriosclerosis based on the acquired blood vessel area. Each of the fundus image photographing devices 11A and 11B photographs the fundus image of the subject eye.

As one example, a personal computer (hereinafter, referred to as a "PC") is employed as the mathematical model construction device 1 of the this embodiment. The mathematical model construction device 1 trains the mathematical model by using the fundus image (hereinafter, referred to as a "training fundus image") acquired by the fundus image photographing device 11A and using the blood vessel image that indicates at least one of the arteriole and the venule in the training fundus image, so as to construct the mathematical model, which will be described in detail later. However, a device serving as the mathematical model construction device 1 is not limited to the PC. For example, the fundus image photographing device 11A may serve as the mathematical model construction device 1. Further, processors of several devices (for example, a CPU of the PC and a CPU 13A of the fundus image photographing device 11A) may work together to construct the mathematical model.

Further, a PC is employed as the fundus image processing device 21 of this embodiment. However, a device serving as the fundus image processing device 21 is not limited to the PC. For example, the fundus image photographing device 11B or a server may serve as the fundus image processing device 21. In a case in which the fundus image photographing device 11B serves as the fundus image processing device 21, the fundus image photographing device 11B photographs the fundus image and then acquires the blood vessel image and the blood vessel area of the blood vessel within the photographed fundus image. Further, the fundus image photographing device 11B may output the subject index based on the acquired blood vessel area. A mobile device such as a tablet and a smartphone may serve as the fundus image processing device 21. Processors of several devices (for example, a CPU of the PC and a CPU 13B of the fundus image photographing device 11B) may work together to execute various processing.

In this embodiment, a configuration that employs a CPU as one example of a processor (controller) that executes various processing is exemplarily described. However, it should be obvious that a processor other than the CPU may be employed in at least a part of each device. For example, a GPU may be employed as the processor to accelerate the processing.

The mathematical model construction device 1 is now described. The mathematical model construction device 1 is disposed in, for example, a manufacturer or the like that provides an operator with the fundus image processing device 21 or a fundus image processing program. The mathematical model construction device 1 is provided with a control unit 2 that executes various control processing, and a communication interface 5. The control unit 2 includes a CPU 3 serving as a processor (controller), and a storage device 4 that can store a program, data, and the like. The storage device 4 stores a mathematical model construction program for executing a mathematical model construction processing (see FIG. 3) described below. The communication interface 5 connects the mathematical model construction device 1 to other device (for example, the fundus image photographing device 11A, the fundus image processing device 21, and the like).

The mathematical model construction device 1 is connected to an operation unit 7 and a display device 8. The operation unit 7 is operated by an operator that inputs various instructions into the mathematical model construction device 1. For example, at least one of a keyboard, a mouse, and a touch panel may be employed as the operation unit 7. Further, a microphone or the like may be employed together with or instead of the operation unit 7 for inputting various instructions. The display device 8 displays various images. Various devices (for example, at least one of a monitor, a display, and a projector) that can display images may be employed as the display device 8.

The mathematical model construction device 1 acquires the data of the fundus image (hereinafter, also simply referred to as a "fundus image") from the fundus image photographing device 11A. The mathematical model construction device 1 may acquire the data of the fundus image from the fundus image photographing device 11A through, for example, at least one of wired communication, wireless communication, and a detachable storage medium (for example, USB memory).

The fundus image processing device 21 is now described. The fundus image processing device 21 is disposed in, for example, facilities (for example, hospitals, medical check facilities, or the like) that diagnose or examine a subject. The fundus image processing device 21 is provided with a control unit 22 that executes various control processing, and a communication interface 25. The control unit 22 includes a CPU 23 serving as a processor (controller), and a storage device 24 that can store a program, data, and the like. The storage medium 24 stores a fundus image processing program for executing a fundus image processing described below (see FIG. 4). The fundus image processing program includes a program that executes the mathematical model constructed by the mathematical model construction device 1. The communication interface 25 connects the fundus image processing device 21 to other device (for example, the fundus image photographing device 11B, the mathematical model construction device 1, and the like).

The fundus image processing device 21 is connected to an operation unit 27 and a display device 28. Various devices may be employed as the operation unit 27 and the display device 28, similar to the operation unit 7 and the display device 8 described above.

The fundus image processing device 21 acquires the fundus image from the fundus image photographing device 11B. The fundus image processing device 21 may acquire the fundus image from the fundus image photographing device 11B through, for example, at least one of wired communication, wireless communication, and a detachable storage medium (for example, USB memory). The fundus image processing device 21 may acquire a program or the like that executes the mathematical model constructed by the mathematical model construction device 1, through wired and/or wireless communication.

The fundus image photographing devices 11 (11A and 11B) are now described. Various devices that photograph the fundus image of the subject eye can be employed as the fundus image photographing device 11. As one example, the fundus image photographing device 11 employed in this embodiment is a fundus camera that is capable of photographing a two-dimensional color front image of the fundus using visible light. Thus, a processing for acquiring the blood vessel image and a processing for acquiring the blood vessel area, which are described later, can be appropriately executed based on the color fundus image. However, a device other than the fundus camera (for example, an optical coherence tomography (OCT) device, a scanning laser ophthalmoscope (SLO), or the like) may be employed. The fundus image may be a two-dimensional front image generated by photographing the fundus of the subject eye from the front side thereof, or a three-dimensional image of the fundus.

The fundus image photographing device 11 is provided with a control unit 12 (12A, 12B) that executes various control processing, and a fundus image photographing unit 16 (16A, 16B). The control unit 12 includes a CPU 13 (13A, 13B) serving as a processor, and a storage device 14 (14A, 14B) that can store a program, data, or the like. The fundus image photographing unit 16 includes an optical member for photographing the fundus image of the subject eye. In a case in which the fundus image photographing device 11 executes at least a part of the fundus image processing described below (see FIG. 4), the storage device 14 stores at least a part of the fundus image processing program for executing the fundus image processing.

A mathematical model construction processing executed by the mathematical model construction device 1 is described with reference to FIG. 2 and FIG. 3. The mathematical model construction processing is executed by the CPU 3 in accordance with the mathematical model construction program stored in the storage device 4.

In the mathematical model construction processing, the mathematical model is trained by a training data set, so that the mathematical model into which the fundus image is input for outputting the blood vessel image is constructed. The training data set includes an input data (input training data) and an output data (output training data). The mathematical model outputs the blood vessel image based on various images. The type of the training data set used for training the mathematical model is determined in response to the type of the fundus image to be input into the mathematical model. In the following description, as one example, a configuration is described that inputs the two-dimensional color front image as an input image photographed by the fundus camera, into the mathematical model so as to cause the mathematical model to output the blood vessel image.

Figure 2:
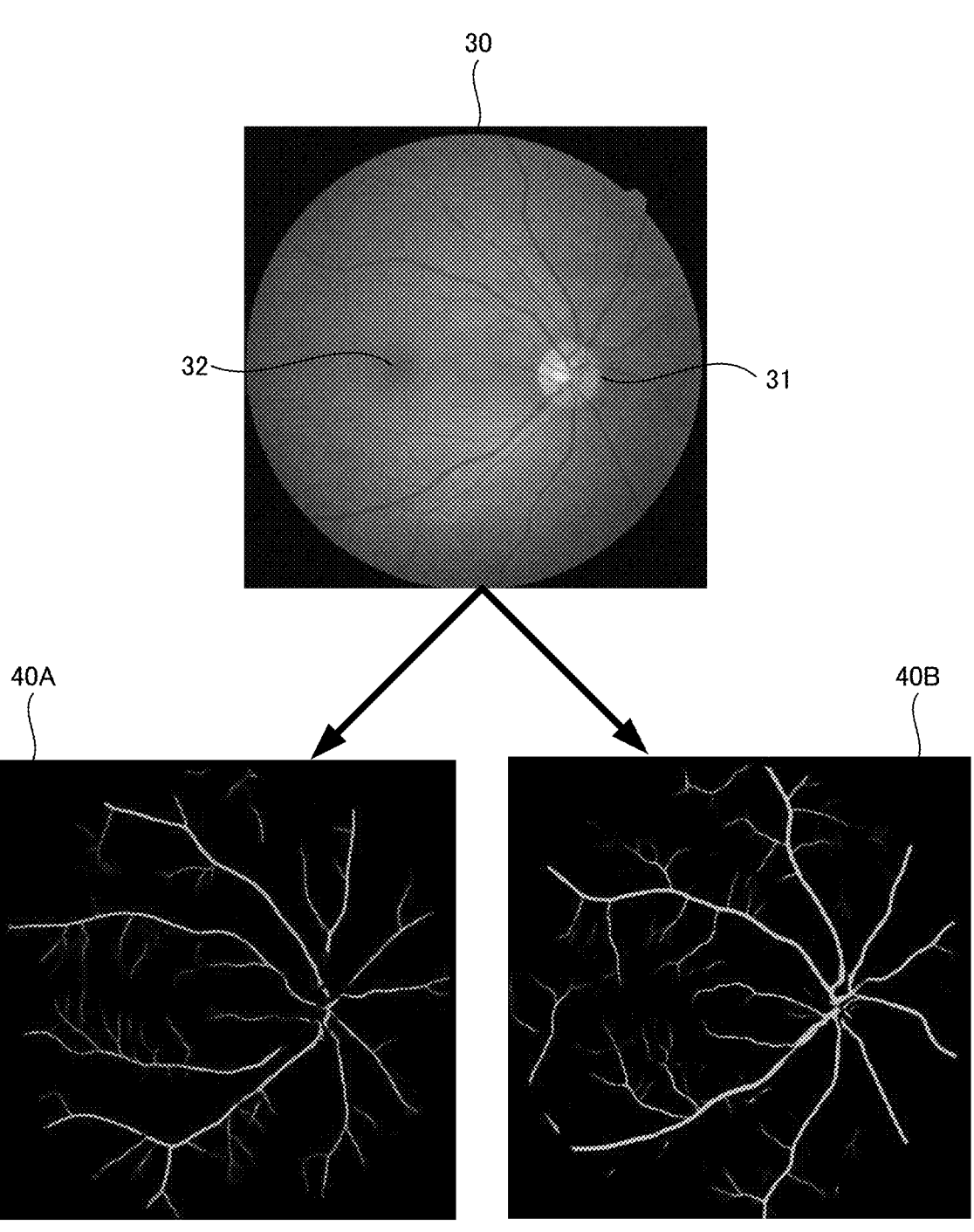
FIG. 2 shows examples of a fundus image 30, and blood vessel images 40A and 40B illustrating a blood vessel in the fundus image 30.
Figure 3:
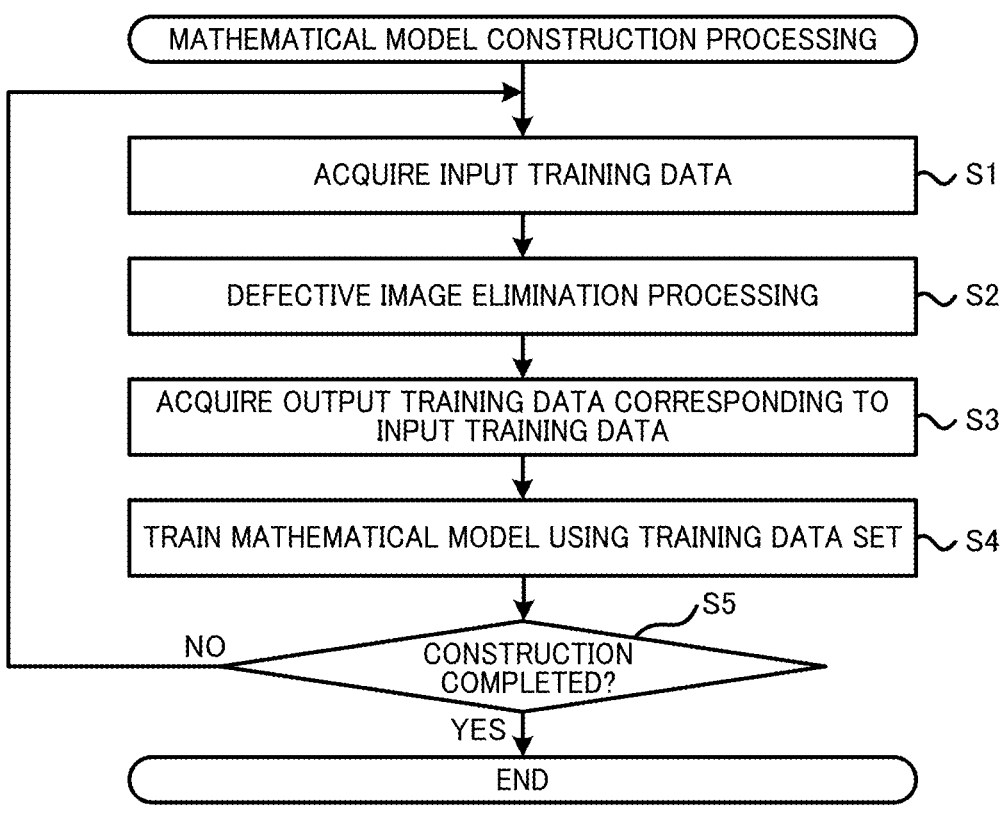
FIG. 3 is a flowchart illustrating a mathematical model construction processing executed by the mathematical model construction device 1.

FIG. 2 shows examples of the input training data and the output training data when causing the mathematical model to output the blood vessel image based on the two-dimensional color front image as an input image. In the example shown in FIG. 2, the fundus image 30, which is a two-dimensional color front image photographed by the fundus image photographing device (a fundus camera in this embodiment) 11A, is set as the input training data. In this embodiment, the image region of the fundus image 30 used as the input training data includes both of an optic papilla 31 and a macula 32 of the subject eye. Blood vessel images 40A and 40B indicating at least one of the arteriole and the venule in the fundus image 30 serving as the input training data, are set as the output training data.

In the example shown in FIG. 2, the blood vessel image 40A of the arteriole in the fundus image 30 and the blood vessel image 40B of the venule in the fundus image 30 are separately prepared. However, one single blood vessel image that shows both of the arteriole and the venule may be used as the output training data. In a configuration that causes the mathematical model to output only the blood vessel image of the arteriole, the blood vessel image 40A of the arteriole may be only used as the output training data. Similarly, in a configuration that causes the mathematical model to output only the blood vessel image of the venule, the blood vessel image 40B of the venule may be only used as the output training data.

One example of a method for generating the blood vessel images 40A and 40B used as the output training data is now described. In this embodiment, a preprocessing mathematical model that outputs blood vessel image serving as a reference for generating the output training data (hereinafter, referred to as a "base blood vessel image") is constructed in advance. The preprocessing mathematical model is trained by the fundus image serving as the input training data and the base blood vessel image, which is manually generated by an operator, serving as the output training data. When training the preprocessing mathematical model, the operator operates the operation unit 7 while referring to the fundus image photographed by the fundus image photographing device 11A and inputs an instruction for generating the base blood vessel image, into the mathematical model construction device 1. The CPU 3 of the mathematical model construction device 1 generates the base blood vessel image in response to the instruction that is input by the operator and then trains the mathematical model using the fundus image and the base blood vessel image so as to construct the preprocessing mathematical model. The CPU 3 inputs the fundus image 30 into the preprocessing mathematical model to output the base blood vessel image and then causes the display device 8 to display the base blood vessel image. The operator operates the operation unit 7 while referring to the displayed base blood vessel image, and inputs an instruction for modifying the base blood vessel image into the mathematical model construction device 1. The CPU 3 modifies the base blood vessel image in response to the instruction and thus generates the blood vessel images 40A and 40B. As a result, the blood vessel images 40A and 40B that precisely show the blood vessel compared to the base blood vessel image can be obtained.

However, the method for generating the blood vessel images 40A and 40B may be changed. For example, the CPU 3 may directly generate the blood vessel images 40A and 40B in response to an instruction that is input by the operator without using the preprocessing mathematical model.

A mathematical model construction processing is now described with reference to FIG. 3. The CPU 3 acquires the fundus image 30 photographed by the fundus image photographing device 11A, as the input training data (S1). In this embodiment, the data of the fundus image 30 is generated by the fundus image photographing device 11A and then acquired by the mathematical model construction device 1. However, the CPU 3 may acquire the data of the fundus image by acquiring a signal (for example, a light receiving signal received by a light receiving element), which is a basis for generating the fundus image 30, from the fundus image photographing device 11A, and then generating the fundus image based on the acquired signal.

Next, the CPU 3 executes a defective image elimination processing (S2). In the defective image elimination processing, the CPU 3 eliminates the fundus image 30 of which a focusing score in photographing is less than a criterion, from the input training data used for training the mathematical model. In the fundus image 30 of which the focusing score is less than a criterion, an area of the blood vessel in the fundus image 30 is larger than the actual blood vessel area.

Thus, the accuracy of the blood vessel image to be output by the trained mathematical model is improved through the defective image elimination processing. In a case in which the CPU 3 eliminates the fundus image 30 acquired in S1, from the input training data, the following S3 to S5 described below are omitted.

As one example, in this embodiment, the CPU 3 executes an edge detection processing to the fundus image 30 acquired in S1 through an image processing and then eliminates the fundus image 30 of which the edge sharpness is less than a threshold, from the input training data. In the fundus image 30 of which the focusing score is low, the edge of the image is unsharp. Thus, by eliminating the fundus image 30 of which the edge sharpness is less than the threshold, only the fundus image 30 of which the focusing score is high is appropriately used as the input training data.

The CPU 3 may use the fundus image 30 of which the focusing score is the highest, as the input training data, among a plurality of the fundus images 30 generated by photographing the fundus of the single subject eye while changing the focus. Also in this case, the accuracy of the blood vessel image to be output by the mathematical model is appropriately improved.

Instead of the processing of S2, or alternatively together with the processing of S2, the fundus image 30 which is defective due to either of a photographing error, opacity of optic media of the subject eye, cataract of the subject eye, and an artifact, may be eliminated from the input training data used for training the mathematical model. In this case, the accuracy of the blood vessel image to be output by the trained mathematical model is further improved.

Next, the CPU 3 acquires the blood vessel images 40A and 40B (the output training data) corresponding to the fundus image 30 (the input training data) acquired in S1 (S3). The example of the method for generating the blood vessel images 40A and 40B based on the fundus image 30 is as described above.

Next, the CPU 3 trains the mathematical model using the training data set by the machine learning algorithm (S4). As the machine learning algorithm, for example, a neural network, a random forest, a boosting, a support vector machine (SVM), and the like are generally known.

The neural network is a technique that imitates the behavior of a neuron network of a living organism. Examples of the neural network include a feedforward neural network, a radial basis function (RBF) network, a spiking neural network, a convolutional neural network, a recurrent neural network (a recurrent neural network, a feedback neural network, and the like), a probabilistic neural network (a Boltzmann machine, a Bayesian network, and the like).

The random forest is a method to generate multiple decision trees, by performing learning on the basis of training data that is randomly sampled. When the random forest is used, branches of a plurality of the decision trees learned in advance as discriminators are followed, and an average (or a majority) of results obtained from the decision trees is calculated.

The boosting is a method to generate a strong discriminator by combining a plurality of weak discriminators. By causing sequential learning of simple and weak discriminators, the strong discriminator is constructed.

The SVM is a method to configure two-class pattern discriminators using linear input elements. For example, the SVM learns linear input element parameters from training data, using a reference (a hyperplane separation theorem)

that calculates a maximum margin hyperplane at which a distance from each of data points is the maximum.

The mathematical model indicates, for example, a data structure for predicting a relationship between input data and output data. The mathematical model is constructed as a result of training using the training data set. As described above, the training data set is a set of the input training data and the output training data. For example, as a result of the training, correlation data (for example, weight) between the inputs and outputs is updated.

In this embodiment, a multi-layer neural network is employed as the machine learning algorithm. The neural network includes an input layer for inputting data, an output layer for generating data to be predicted, and one or more hidden layers between the input layer and the output layer. A plurality of nodes (also known as units) is disposed in each layer. Specifically, a convolutional neural network (CNN) that is one example of the multi-layer neural network is employed in this embodiment. However, other machine learning algorithm may be employed. For example, generative adversarial networks (GAN) using two competitive neural networks may be employed as the machine learning algorithm.

The processing of S1 to S4 is repeated until the construction of the mathematical model is completed (S5: NO). When the construction of the mathematical model is completed (S5: YES), the mathematical model construction processing is finished. The program and the data for executing the constructed mathematical model are installed in the fundus image processing device 21.

Fundus image processing A fundus image processing in this embodiment is described with reference to FIG. 4 and FIG. 5. In the fundus image processing in this embodiment, the mathematical model trained by the machine learning algorithm is used to acquire blood vessel images 60A and 60B (see FIG. 5) indicating the blood vessel in the fundus image 50 (see FIG. 5) and acquire the blood vessel area based on the blood vessel images 60A and 60B. Further, a subject index that indicates at least one of an estimated age of the subject, a degree of hypertension, and a degree of arteriosclerosis, is output based on the blood vessel area. The fundus image processing exemplarily shown in FIG. 4 is executed by the CPU 23 of the fundus image processing device 21 in accordance with the fundus image processing program stored in the storage device 24.

Figure 4:
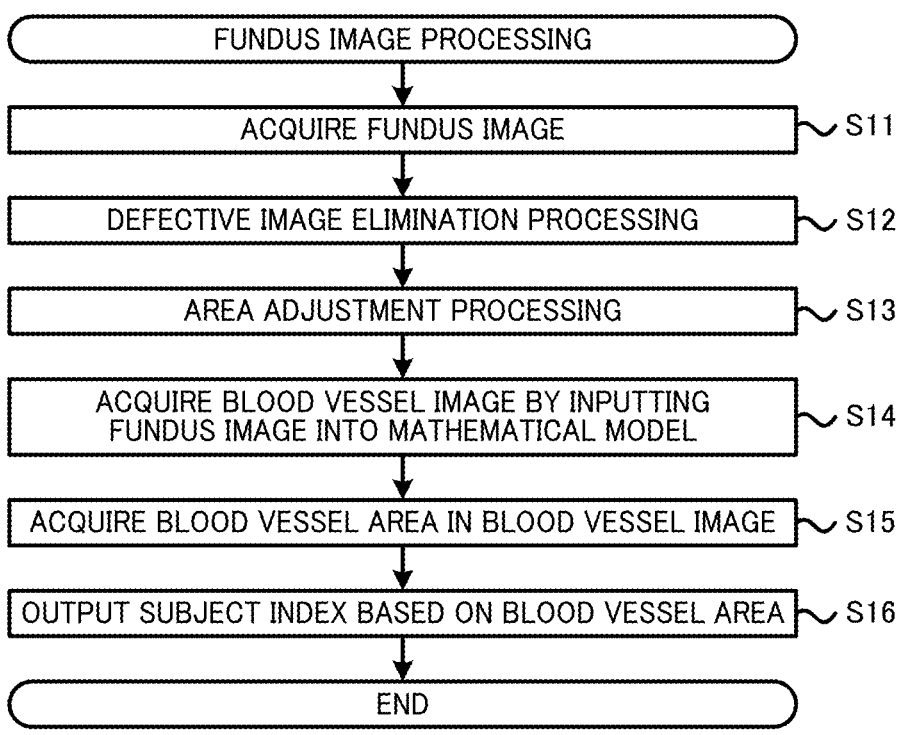
FIG. 4 is a flowchart illustrating a fundus image processing executed by the fundus image processing device 21.
Figure 5:
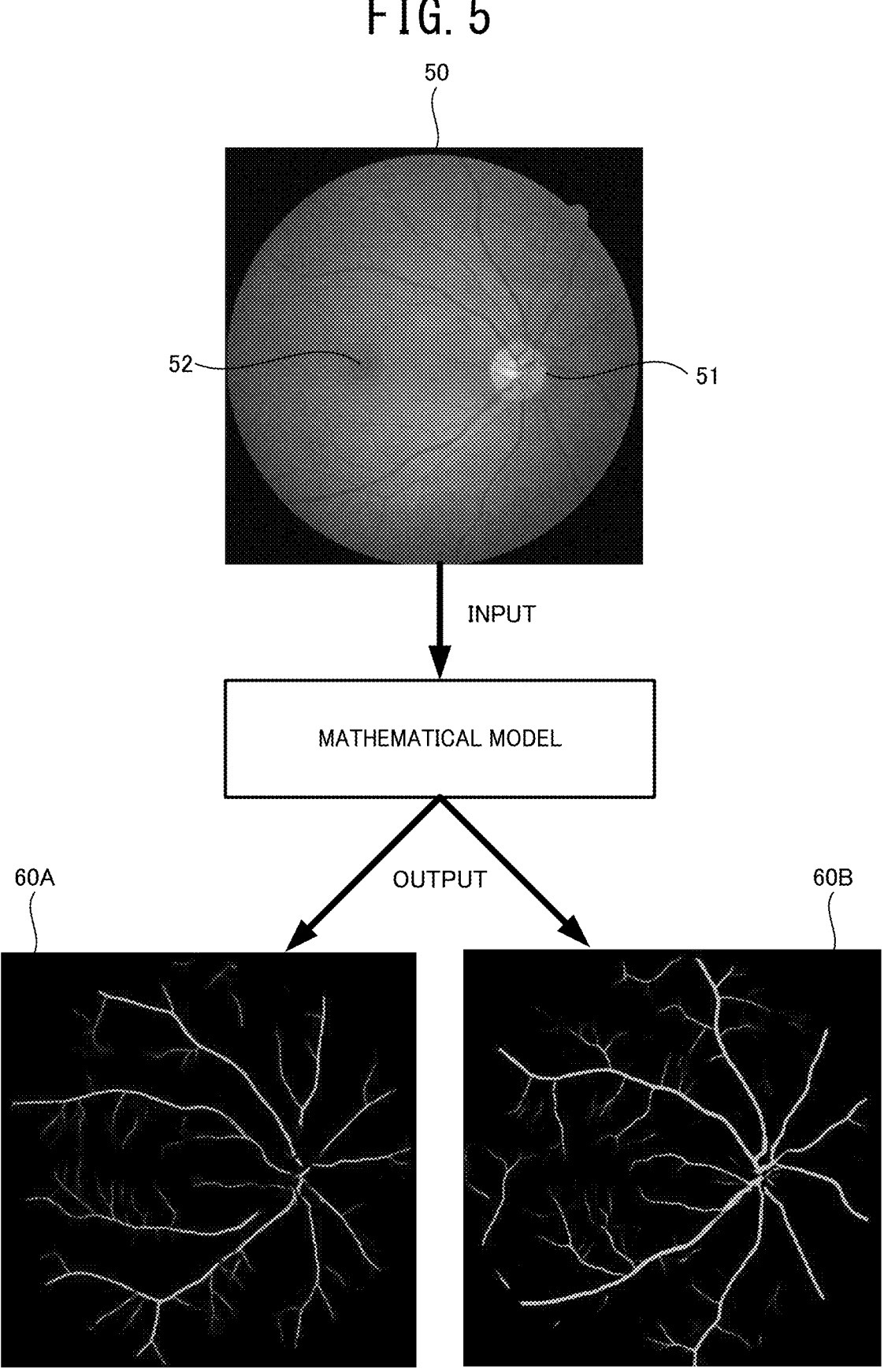
FIG. 5 is a view for describing an example of a method for acquiring blood vessel images 60A and 60B from a fundus image 50, using the mathematical model.

As shown in FIG. 4, the CPU 23 acquires the fundus image 50 (see FIG. 5), which is a two-dimensional color front image, photographed by the fundus image photographing device (the fundus camera in this embodiment) 11B (S11). The fundus image 50 acquired in S11 is the same type of image (namely, the image photographed by the same type of the fundus image photographing device) as the fundus image 30 (see FIG. 2) used as the input training data in training the mathematical model. In this embodiment, the image region the fundus image 50 acquired in S11 includes both of an optic papilla 51 and a macula 52 of the subject eye.

Next, the CPU 23 executes a defective image elimination processing (S12). In the defective image elimination processing, the CPU 23 eliminates the fundus image 50 of which a focusing score in photographing is less than a criterion, from the data to be input into the mathematical model. Similar to the fundus image 30, in the fundus image 50 of which the focusing score is less than a criterion, an area of the blood vessel in the fundus image 50 is larger than the actual blood vessel area. Thus, the accuracy of each of the blood vessel images 60A and 60B to be output by the mathematical model in S14 described below is improved through the defective image elimination processing. In a case in which the CPU 23 eliminates the fundus image 50 acquired in S11 from the data in S12, the following S13 to S16 described below are omitted.

A specific method in the defective image elimination processing (S12) may be appropriately selected. As one example, in this embodiment, similar to S2 in the above-described mathematical model construction processing (see FIG. 3), the CPU 23 executes an edge detection processing to the fundus image 50 acquired in S11 and then eliminates the fundus image 50 of which the edge sharpness is less than a threshold, from the data to be input into the mathematical model. The CPU 23 may use the fundus image 50 of which the focusing score is the highest, as the fundus image 50 to be input into the mathematical model, among a plurality of the fundus images 50 generated by photographing the fundus of the single subject eye while changing the focus. Instead of the processing of S12, or alternatively together with the processing of S12, the fundus image 50 which is defective due to either of a photographing error, opacity of optic media of the subject eye, cataract of the subject eye, and an artifact, may be eliminated from the data to be input into the mathematical model.

Next, the CPU 23 executes an area adjustment processing (S13). In the area adjustment processing, the CPU 23 adjusts an area of the image region within the fundus image 50, which has been acquired in S11, to be input into the mathematical model, so as to bring the area close to a target value. As a result, the area of the image region from which the blood vessel area is acquired is uniformized, so that an influence of the individual difference of the subject eyes and the difference of the photographing ways can be suppressed. In this embodiment, the image region is adjusted such that the optic papilla 51 and the macula 52 are included in the image region of the fundus image 50 to be input into the mathematical model.

As one example, in this embodiment, the CPU 23 acquires information relating to the eye axial length of the subject eye to be photographed, and uniformizes the area of the image region to be input into the mathematical model, within the fundus image 50 in response to the eye axial length. However, a specific method in the area adjustment processing may be appropriately changed. For example, the CPU 23 may set the region including the fundus blood vessel from the optic papilla 51 to the N-th (N is a natural number set in advance) branch point within the fundus blood vessel in the fundus image 50, as the image region to be input into the mathematical model.

Next, the CPU 23 inputs the fundus image 50 into the mathematical model trained by the machine learning algorithm so as to acquire the blood vessel images 60A and 60B showing at least one of the arteriole and the venule in the fundus image 50 (S14). As shown in FIG. 5, in this embodiment, the blood vessel image 60A of the arteriole in the fundus image 50 and the blood vessel image 60B of the venule in the fundus image 50 are separately acquired through the mathematical model. However, one single blood vessel image that shows both of the arteriole and the venule may be output by the mathematical model. Further, the mathematical model may output only one of the blood vessel image 60A of the arteriole and the blood vessel image 60B of the venule.

Next, the CPU 23 acquires the blood vessel area, which is an area of the blood vessel (the arteriole or the venule in this embodiment) in each of the blood vessel images 60A and 60B acquired in S14 (S15). The method for acquiring the blood vessel area from the blood vessel image 60A or 60B may be appropriately selected. As one example, in this embodiment, the number of pixels that form the blood vessel in each of the blood vessel images 60A and 60B is acquired as the blood vessel area. However, the method for acquiring the blood vessel area may be changed. For example, a mathematical model into which the blood vessel image 60A or 60B is input for outputting the blood vessel area may be employed. In this case, the mathematical model may be trained in advance by the blood vessel image serving as the input training data and the blood vessel area serving as the output training data.

Further, the CPU 23 may adjust the area of the image region of the blood vessel image 60A or 60B from which the blood vessel area is acquired in S15, instead of S13 that adjusts the area of the image region of the fundus image 50 to be input into the mathematical model. In this case, a method for adjusting the area of the blood image 60A or 60B may employ the method similar to the method in S13 described above.

Next, the CPU 23 outputs the subject index that indicates at least one of an estimated age of the subject for which the fundus image 50 is photographed, a degree of hypertension, and a degree of arteriosclerosis, based on the blood vessel area acquired in S15 (S16).

Figure 9:
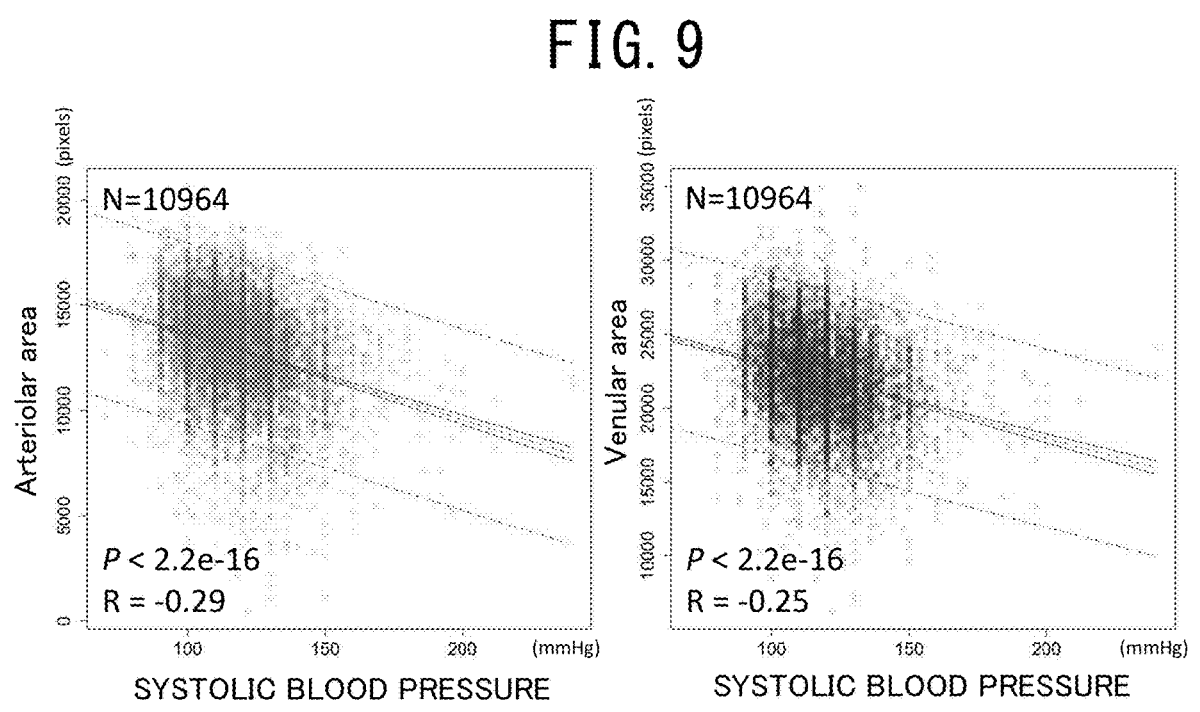
Figure 10:
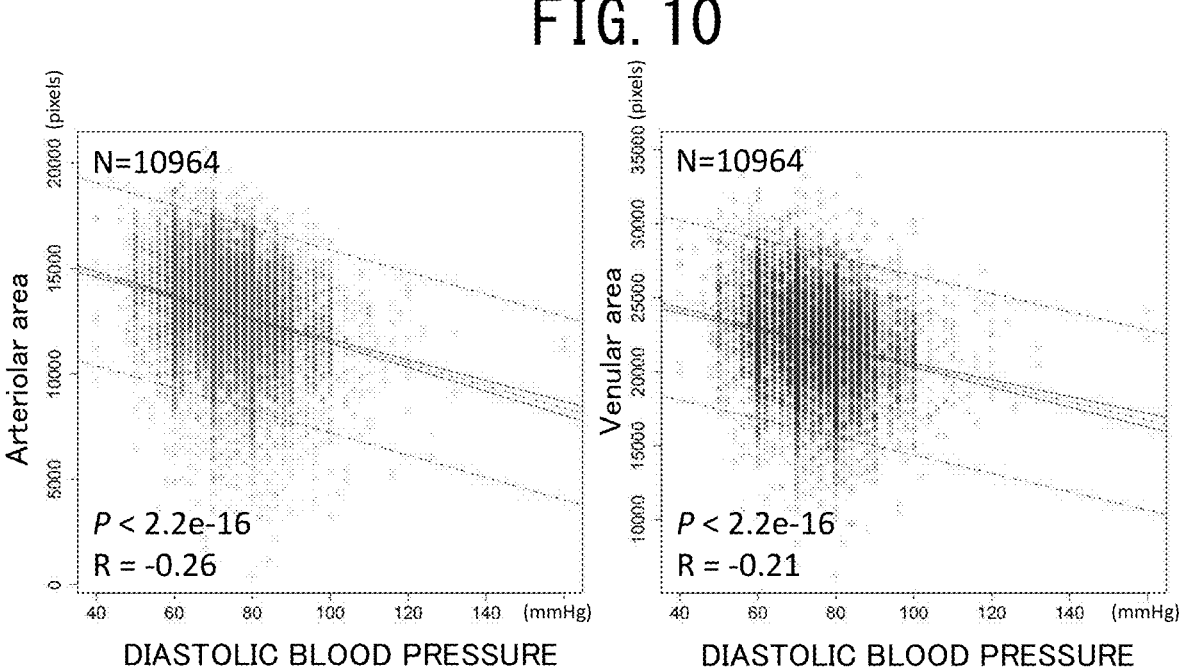
FIG. 10 shows graphs relating to the arteriolar area and the venular area as the diastolic blood pressure is set in the horizontal axis and the blood vessel area is set in the vertical axis.
Figure 11:
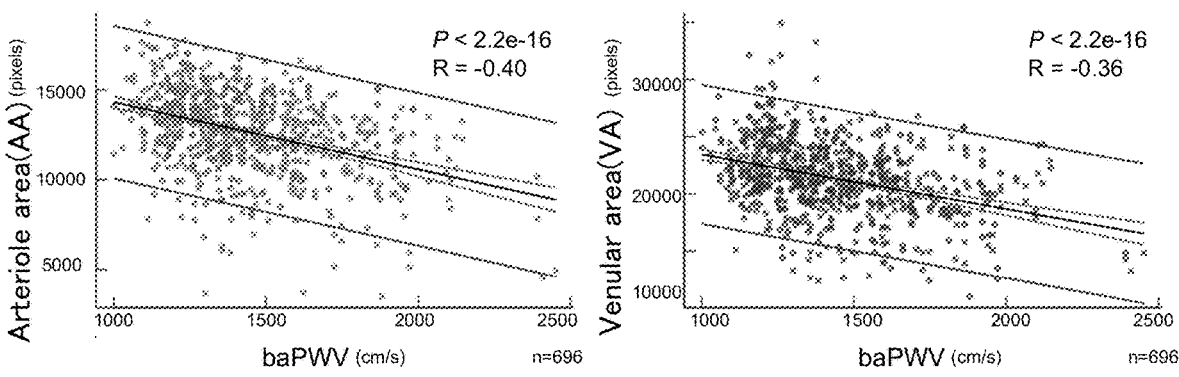
FIG. 11 shows graphs relating to the arteriolar area and the venular area as the measured value of baPWV (brachial-ankle pulse wave velocity) is set in the horizontal axis and the blood vessel area is set in the vertical axis.
Figure 13:
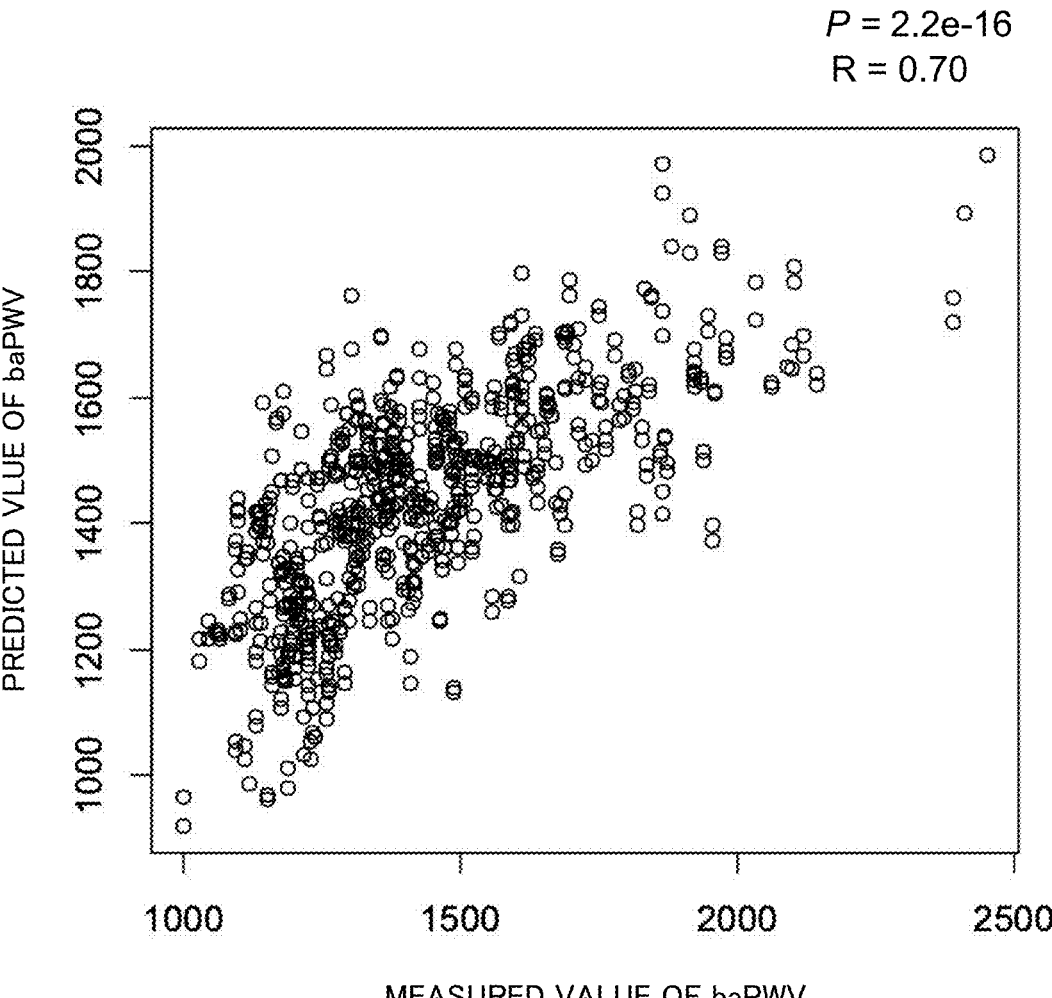
FIG. 13 shows a graph of the predicted value of the baPWV predicted based on the arteriolar area, sex, systolic blood pressure and age, and the measured value of the baPWV

In the following description, new knowledge that the present inventors have obtained based on the data of many subjects is described, and also one example of a method for outputting the subject index based on the blood vessel area is described. FIG. 6 to FIG. 10 show the data based on 5,600 subjects (male: 3,608; female: 1,997) in which the number of the subject eyes is 10,586; the number of the fundus images 50 is 10,964; the average age of the subjects is 49.4±9.6 years old; the average systolic blood pressure of the subjects is 117.6±16.1 mmHg; and the average diastolic blood pressure of the subjects is 74.0±11.0 mmHg. Further, FIG. 11 to FIG. 13 show the data based on 372 subjects in which the number of the subject eyes is 696 (male subject eyes: 542; female subject eyes: 154); the number of the fundus images 50 is 696; the average age of the subjects is 53.7±10.6 years old; the average systolic blood pressure of the subjects is 122.1±15.0 mmHg; and the average diastolic blood pressure of the subjects is 76.1±10.3 mmHg.

Figure 6:
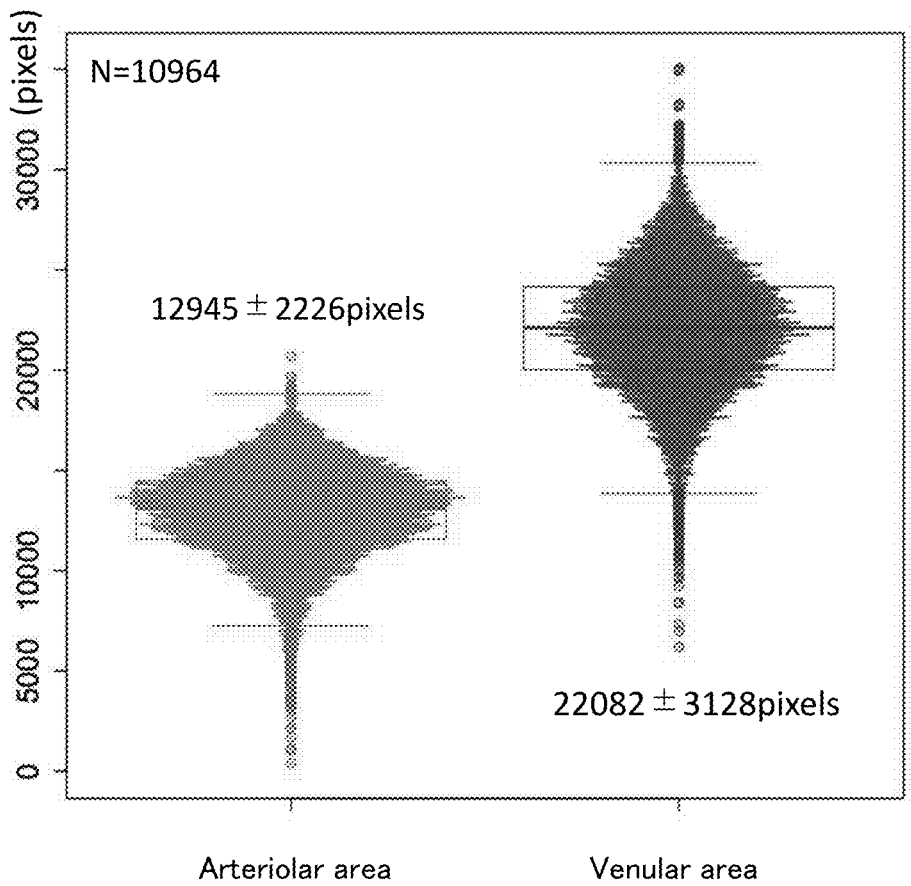
FIG. 6 shows a graph of a distribution of a blood vessel area of the arteriole (an arteriolar area) and a distribution of the blood vessel area of the venule (a venular area).

The distributions of the blood vessel area of the arteriole (Arteriolar area) and the blood vessel area of the venule (Venular area) and the area ratio are now described with reference to FIG. 6. As shown in FIG. 6, the arteriolar area is generally smaller than the venular area. The ratio is "the arteriolar area:the venular area=approximately 1:1.7". The ratio of the arteriolar area relative to the whole area of the fundus image 50 is approximately 2.6% and the ratio of the venular area relative to the whole area of the fundus image 50 is approximately 4.5%.

Figure 7:
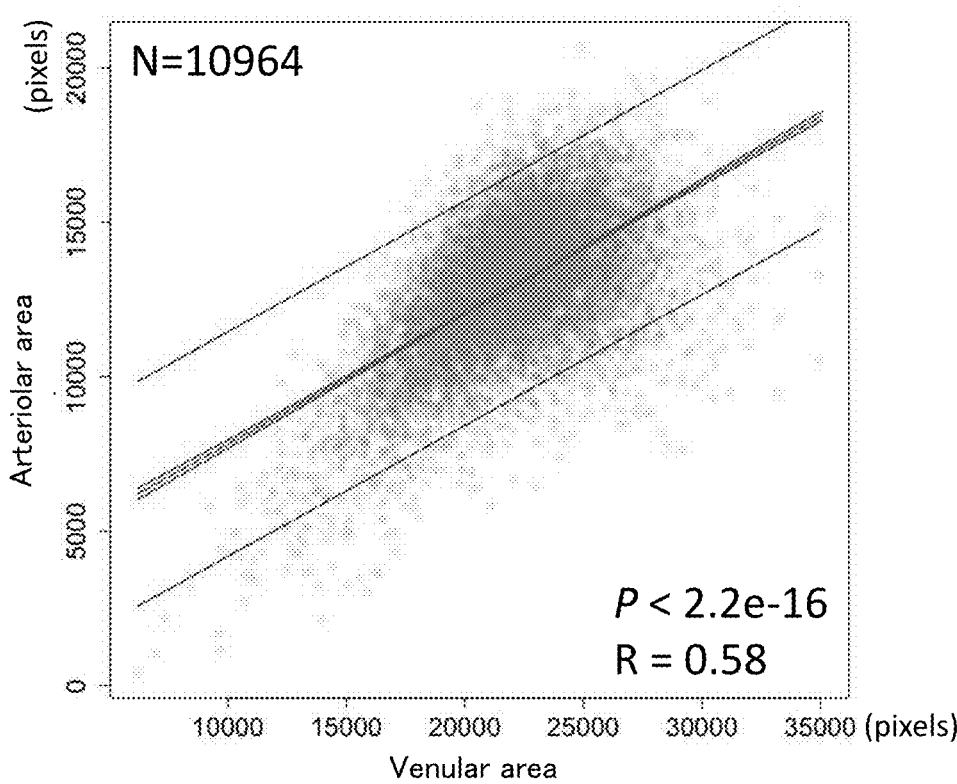
FIG. 7 shows a graph of the arteriolar area and the venular area of each subject eye as the venular area is set in the horizontal axis and the arteriolar area is set in the vertical axis.

A correlation between the arteriolar area and the venular area is now described with reference to FIG. 7. Each two adjacent lines diagonally passing the center portions of the graphs in FIG. 7 to FIG. 11 denote the 95% confidential interval. Further, each two lines diagonally passing the outsides of the 95% confidential intervals in FIG. 7 to FIG. 11 denote the 95% prediction interval. As shown in FIG. 7, there is a correlation between the arteriolar area and the venular area. The correlation coefficient R between the arteriolar area and the venular area is 0.58, which is a moderate positive correlation.

Figure 8:
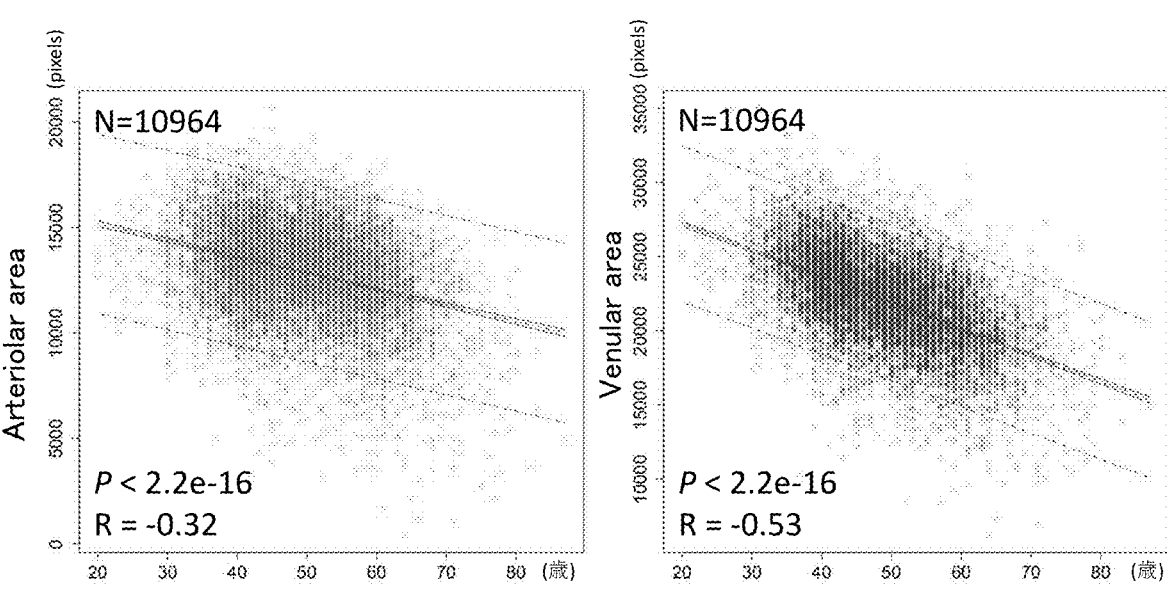
FIG. 8 shows graphs relating to the arteriolar area and the venular area as the age is set in the horizontal axis and the blood vessel area is set in the vertical axis.

A correlation between the arteriolar area and the age, and a correlation between the venular area and the age are now described with reference to FIG. 8. The correlation coefficient between the arteriolar area and the age of the subject is −0.32. The correlation coefficient between the venular area and the age of the subject is −0.53. There are negative correlations between the arteriolar area and the age and between the venular area and the age. The correlation between the venular area and the age is stronger than the correlation between the arteriolar area and the age.

Accordingly, in this embodiment, a calculation formula or a table is set for estimating the age of the subject from the venular area based on the relation between the venular area and the age acquired from each subject. The CPU 23 applies the venular area acquired in S15 into the calculation formula or the table so as to output the subject index indicating the estimated age of the subject.

The method for outputting the subject index indicating the estimated age of the subject may be changed. For example, a calculation formula or a table for estimating the age of the subject from the venular area and the arteriolar area may be set based on the data relating to the subjects. The CPU 23 may apply the arteriolar area and the venular area acquired in S15 into the calculation formula or the table so as to output the subject index indicating the estimated age of the subject. Or alternatively, the CPU 23 may output the subject index indicating the estimated age of the subject based on the ratio of the arteriolar area and the venular area.

A correlation between the arteriolar area and the systolic blood pressure and a correlation between the venular area and the systolic blood pressure are now described with reference to FIG. 9. A correlation coefficient between the arteriolar area and the systolic blood pressure of the subject is −0.29. Further, a correlation coefficient between the venular area and the systolic blood pressure of the subject is −0.25. There are negative correlations between the arteriolar area and the systolic blood pressure and between the venular area and the systolic blood pressure. The correlation between the arteriolar area and the systolic blood pressure is stronger than the correlation between the venular area and the systolic blood pressure. As described above, there is also the correlation between the blood vessel area and the age of the subject.

Accordingly, in this embodiment, a calculation formula or a table is set for estimating an index indicating the systolic blood pressure of the subject from the arteriolar area and the age of the subject based on the relation between the arteriolar area, the age, and the systolic blood pressure acquired from each subject. The CPU 23 applies the age of the subject and the arteriolar area acquired in S15 into the calculation formula or the table so as to output the subject index indicating the systolic blood pressure. The age of the subject used for outputting the subject index may be input by an operator, or alternatively the estimated age described above may be input.

The method for outputting the subject index indicating the systolic blood pressure may be changed. For example, a calculation formula or a table for estimating the subject index indicating the systolic blood pressure from the venular area, the arteriolar area and the age may be set based on the data relating to the subjects. The CPU 23 may apply the venular area, the arteriolar area, and the age of the subject into the calculation formula or the table so as to output the subject index indicating the systolic blood pressure. Further, a ratio of the arteriolar area and the venular area may be used to output the subject index indicating the systolic blood pressure.

A correlation between the arteriolar area and the diastolic blood pressure and a correlation between the venular area and the diastolic blood pressure are now described with reference to FIG. 10. A correlation coefficient between the arteriolar area and the diastolic blood pressure of the subject is −0.26. Further, a correlation coefficient between the venular area and the diastolic blood pressure of the subject is −0.21. There are negative correlations between the arteriolar area and the diastolic blood pressure and between the venular area and the diastolic blood pressure. The correlation between the arteriolar area and the diastolic blood pressure is stronger than the correlation between the venular area and the diastolic blood pressure. As described above, there is also the correlation between the blood vessel area and the age of the subject.

Accordingly, in this embodiment, a calculation formula or a table is set for estimating an index indicating the diastolic blood pressure of the subject from the arteriolar area and the age of the subject based on the relation between the arteriolar area, the age, and the diastolic pressure acquired from each subject. The CPU 23 applies the age of the subject and the arteriolar area acquired in S15 into the calculation formula or the table so as to output the subject index indicating the diastolic blood pressure. The age of the subject used for outputting the subject index may be input by an operator, or alternatively the estimated age described above may be input.

The method for outputting the subject index indicating the diastolic blood pressure may be changed. For example, a calculation formula or a table for estimating the subject index indicating the diastolic blood pressure from the venular area, the arteriolar area and the age may be set based on the data relating to the subjects. The CPU 23 may apply the venular area, the arteriolar area and the age of the subject into the calculation formula or the table so as to output the subject index indicating the diastolic blood pressure. Further, a ratio of the arteriolar area and the venular area may be used to output the subject index indicating the diastolic blood pressure.

At least one of the subject index indicating the systolic blood pressure and the subject index indicating the diastolic blood pressure may be output as an index indicating a degree of hypertension of the subject. Further an index indicating a degree of hypertension of the subject (for example, a stepwise index indicating a degree of hypertension to be estimated) may be estimated and output based on at least one of the subject index indicating the systolic blood pressure and the subject index indicating the diastolic blood pressure.

A correlation between the arteriolar area and the PWV (Pulse Wave Velocity) and a correlation between the venular area and the PWV are now described with reference to FIG. 11. The PWV is calculated from a distance between two points on a body surface from which pulse waves are measured, and a time difference between the pulsations. The PWV is calculated from "(blood vessel elasticity modulus× blood vessel wall thickness)/(2×blood vessel diameter× blood density)". The pulse wave becomes faster as the blood vessel is harder, the pulse wave becomes faster as the blood vessel wall is thicker, and the pulse wave becomes faster as the blood vessel diameter is smaller. The PWV has been used as a useful index for arteriosclerosis. In the following description, baPWV (brachial-ankle pulse wave velocity) between the brachial arteriole and the ankle arteriole is used as one example of the PWV.

As shown in FIG. 11, a correlation coefficient between the arteriolar area and the baPWV is −0.40. Further, a correlation coefficient between the venular area and the baPWV is −0.36. There are negative correlations between the arteriolar area and the baPWV and between the venular area and the baPWV. The correlation between the arteriolar area and the baPWV is stronger than the correlation between the venular area and the baPWV.

Correlation between the PWV and either of the arteriolar area (AA), sex, systolic blood pressure and age of the subject are now described with reference to FIG. 12. As shown in FIG. 12, there are correlations between the PWV and not only the arteriolar area but also either of sex, systolic blood pressure and age. Each of the fields with "*" in FIG. 12 shows a correlation based on a predicted value.

A correlation between the predicted value of the baPWV based on the arteriolar area, sex, systolic blood pressure and age, and the measured value of the baPWV is now described with reference to FIG. 13. As shown in FIG. 13, there is a significant positive correlation between the predicted value of the baPWV based on the arteriolar area, sex, systolic blood pressure and age, and the measured value of the baPWV Accordingly, in this embodiment, a calculation formula or a table is set for estimating an index indicating the PWV of the subject (the predicted value) from the arteriolar area, sex, systolic blood pressure, and age, based on the arteriolar area, sex, systolic blood pressure, age, and the measured value of the PWV (for example, baPWV) acquired from each subject. The CPU 23 applies the arteriolar area acquired in S15 and information relating to the age or the like of the subject into the calculation formula or the table so as to output the predicted value of the PWV as one example of the index indicating the degree of arteriosclerosis. The PWV can be relatively easily measured, while the measuring of the PWV needs time (for example, 5 minutes or more). However, the fundus image processing device 21 of this embodiment can appropriately output the index indicating the degree of arteriosclerosis (the predicted value of the PWV) based on the fundus image 50 that can be photographed at a short time.

The method for outputting the index indicating the degree of arteriosclerosis may be changed. For example, in addition to or instead of the arteriolar area, the venular area may be used for outputting the index indicating the degree of arteriosclerosis. Or alternatively, a ratio of the arteriolar area and the venular area may be used for outputting the index indicating the degree of arteriosclerosis. Further, the degree of arteriosclerosis may be output without using at least one of information (sex, blood pressure, and age) other than the blood vessel area. At least one of the arteriolar area, the venular area, and the ratio of the arteriolar area and the venular area may be output as it is as the index indicating the degree of arteriosclerosis.

The technique disclosed in the above-described embodiment is merely an example. Thus, the technique exemplarily described in the embodiment may be modified. For example, the processing that outputs the subject index based on the blood vessel area (see S16 in FIG. 4) may be omitted, and thus the blood vessel area acquired in S15 may be merely output. Also in this case, the operator (for example, a doctor or the like) can appropriately and easily perform the diagnosis of the subject based on the information relating to the blood vessel area to be output.

The processing that acquires the fundus image in S11 shown in FIG. 4 is one example of the step of "acquiring a fundus image". The processing that acquires the blood vessel image in S14 shown in FIG. 4 is one example of the step of "acquiring a blood vessel image". The processing that acquires the blood vessel area in S15 shown in FIG. 4 is one example of the step of "acquiring a blood vessel area".

The processing that outputs the subject index in S16 shown in FIG. 4 is one example of the step of "outputting an index".

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. A non-transitory computer-readable storage medium storing computer-readable instructions that, when executed by a processor of a fundus image processing device that processes a fundus image of a subject eye, cause the fundus image processing device to perform the steps of:

(a) acquiring the fundus image photographed by a fundus image photographing device;

(b) acquiring a blood vessel image that indicates at least one of an arteriole and a venule in the fundus image by inputting the fundus image into a mathematical model trained by a machine learning algorithm;

(c) acquiring a total blood vessel area that is an area of at least one of the arteriole and the venule of the entire blood vessel image acquired in the step of (b), the total blood vessel area being a number of pixels that form the blood vessel in the entire blood vessel image; and (d) outputting an index that indicates at least one of an estimated age of a subject for which the fundus image is photographed, a degree of hypertension, and a degree of arteriosclerosis, based on the total blood vessel area acquired in the step of (c).

2. The non-transitory computer-readable storage medium as defined in claim 1, wherein an image region of the fundus image to be input into the mathematical model is set to include an optic papilla and a macula of a subject eye.

3. The non-transitory computer-readable storage medium as defined in claim 1, wherein the mathematical model is trained by the fundus image of the subject eye photographed in advance, the fundus image serving as an input training data, and the blood vessel image indicating at least one of the arteriole and the venule in the fundus image in the input training data, the blood vessel image serving as an output training data.

4. A fundus image processing device, comprising the non-transitory computer-readable storage medium according to claim 1.

* * * * *